United States Patent [19]

van der Knaap

[11] Plant 4,891

[45] Sep. 28, 1982

[54] CHRYSANTHEMUM NAMED ORANGE WESTLAND

[75] Inventor: Jacques C. M. van der Knaap, De Lier, Netherlands

[73] Assignee: Pan-American Plant Company, Parrish, Fla.

[21] Appl. No.: 193,089

[22] Filed: Oct. 2, 1980

[51] Int. Cl.[3] ..... A01H 5/00

[52] U.S. Cl. ..... Plt./76

[58] Field of Search ..... Plt./74–83

*Primary Examiner*—James R. Feyrer

*Attorney, Agent, or Firm*—Chas. W. Rummler

[57] ABSTRACT

A new and distinct chrysanthemum cultivar originated as a sport developed by radiation of the variety "Westland" and distinguished by the unique and distinct orange coloration of its blooms. This new plant substantially retains the vigorous growth habit and physical characteristics of its parent and differs mainly by its orange color. The title of this application is the European denomination for this variety. In the United States, this variety is marketed as "Westland Orange".

3 Drawing Figures

BACKGROUND OF THE NEW PLANT

This new chrysanthemum variety was developed by me at De Lier, Holland, in 1976 by radiation of the variety "Westland" (U.S. Plant Pat. No. 4,589) and was selected by me for propagation because of the unique and distinctive color of its flowers. This plant was reproduced by me with cuttings of its parent and propagation through successive generations has demonstrated that the novel characteristics of this sport hold true from generation to generation and appear to be firmly fixed. Propagation on a commercial scale is now being done by means of cuttings at West Chicago, Ill.; Cortez, Fla.; and at De Lier, Holland.

DESCRIPTION OF THE DRAWINGS

My new chrysanthemum cultivar is illustrated by the accompanying drawings, of which sheet 1 is a full color photographic rendition of a group of flowers of this plant taken when in full bloom, and sheets 2 and 3 are reproductions of photoprints of the front and back sides, respectively, of typical leaves of this new variety.

DESCRIPTION OF THE NEW PLANT

The following is a detailed description of this new variety of chrysanthemum based upon observations made at West Chicago, Ill., U.S.A., in the summer of 1980, with color designations according to the R.H.S. Colour Chart published by The Royal Horticultural Society of London, England.

THE PLANT

Origin: Sport, by radiation culture.
Parentage: Westland (U.S. Plant Pat. No. 4,589).
Classification:
- *Botanic.*—*Chrysanthemum morifolium.*
- *Commercial.*—Greenhouse chrysanthemum for cut flowers.

Form: Perennial herbaceous bush.
Height: Varies according to culture.
Growth: Strong, vigorous and upright.
Branching: None. Cymose inflorescence on a single stem.
Foliage:
- *Quantity.*—Abundant.

- *Leaf size.*—Length — about 40 to 100 mm. Width — about 20 to 70 mm.
- *Shape.*—Ovate with cleft margins.
- *Surface texture.*—Leathery.
- *Venation.*—Pinnate.
- *Color.*—Upper side — 147A. Under side — 147B.
- *Petioles.*—Length: about 12 to 30 mm.

THE BUD

Form: Globular.
Size: Varies in both diameter and length.
Opening rate: Normal.
Color of florets:
- *When phyllaries first divide.*—164C.
- *When petals begin to unfurl.*—164C.

Phyllaries:
- *Number.*—Approximately 15.
- *Shape.*—Lanceolate.
- *Color.*—138A.

Peduncle:
- *Character.*—Rigid and erect.
- *Length.*—Varies.
- *Surface aspect.*—Canescent.
- *Color.*—138B.

THE FLOWER

Blooming habit: Normally intermittent.
Recommended flowering: Year around with photoperiod control.
Blooms:
- *Size.*—Medium. Diameter — about 60 to 70 mm. Depth — about 12 to 15 mm.

Borne: Cymose on a strong, upright main stem.
Shape: Cup-shaped when bloom first opens, becoming flat when bloom matures.
Florets:
- *Number.*—Many ray florets; few disc florets.
- *Arrangement.*—Imbricated.
- *Form.*—Quill with entire margin, open tip and with rounded-incised apex.
- *Texture.*—Soft.
- *Appearance.*—Satiny.
- *Color.*—Outer florets: upper side — 164C to 164A toward base. Reverse side — 164C. Inner florets: upper side — 164A to 164B toward base. Reverse side — 164A. Central florets: 1C to 1A to 164A at tip.

Flower stem: Strong and upright and of various lengths.
*Color.*—138B.

Persistence: Flowers hang on and dry.

Fragrance: Typical chrysanthemum.

Lasting quality:
*On plant.*—4 weeks.
*As cut flower.*—4 weeks.

REPRODUCTIVE ORGANS

Stamens: Few in number and with syngenesious arrangement.

Pistils: Number — one for each ray floret.

*Styles.*—Color: greenish-yellow.
*Stigmas.*—Color: greenish-yellow.

Ovaries: Inferior bicarpellate.

In all respects, except color, this new variety is substantially the same as its parent "Westland". The distinct and unique orange color, however, distinguishes this variety from all others.

I claim:

1. A new and distinct chrysanthemum cultivar, substantially as herein shown and described, characterized by its unique quill-shaped ray florets of a distinctive orange coloration.

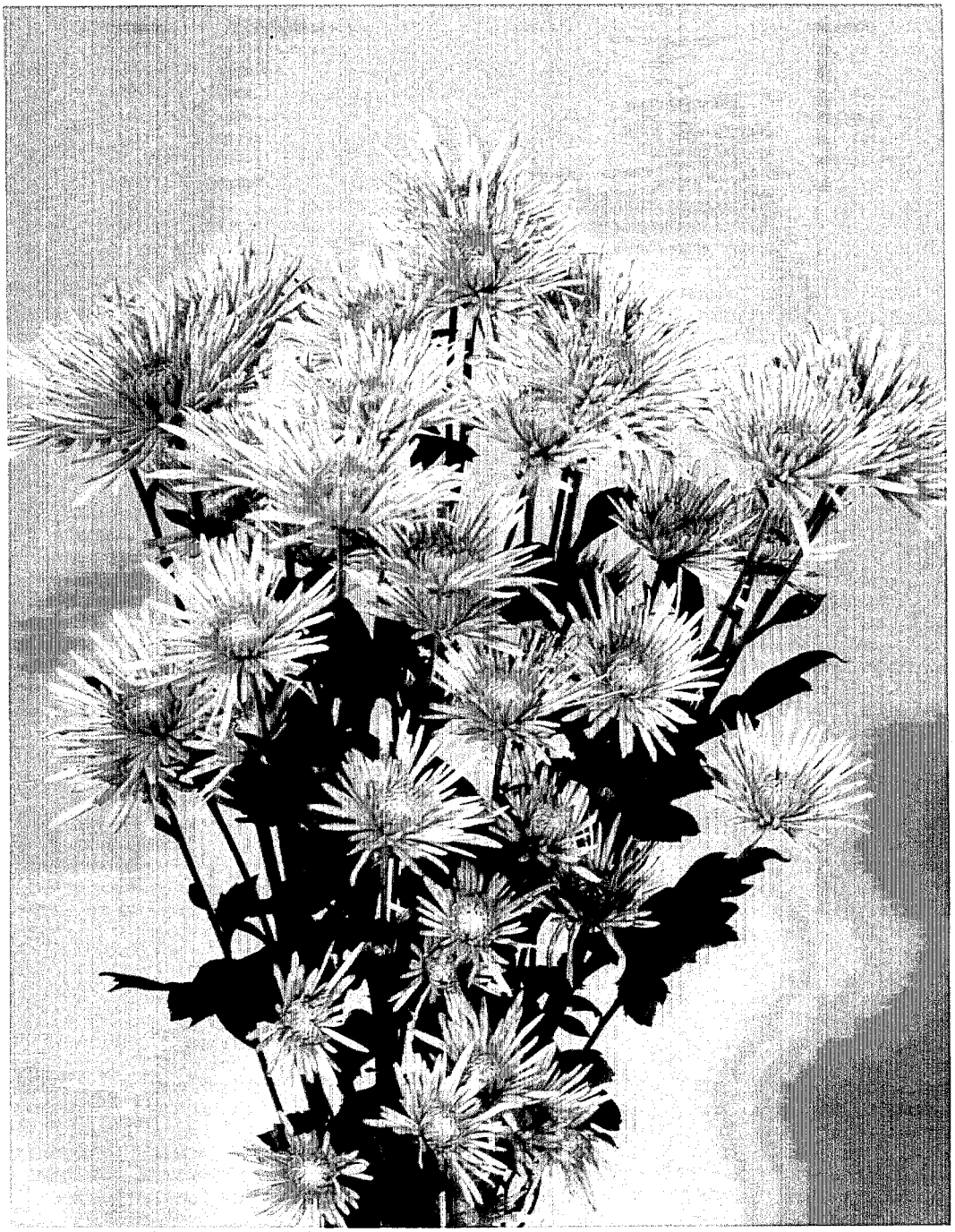

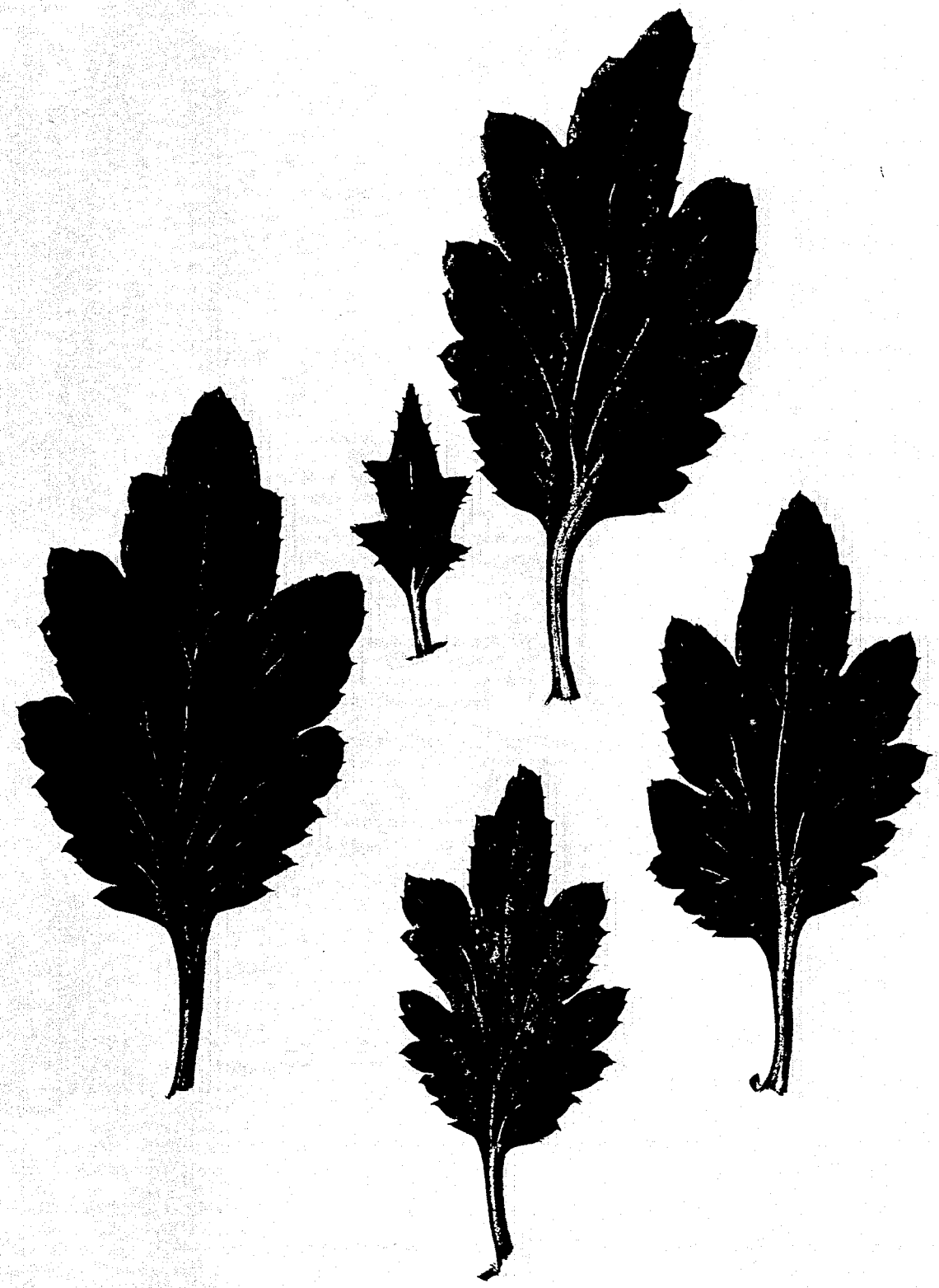

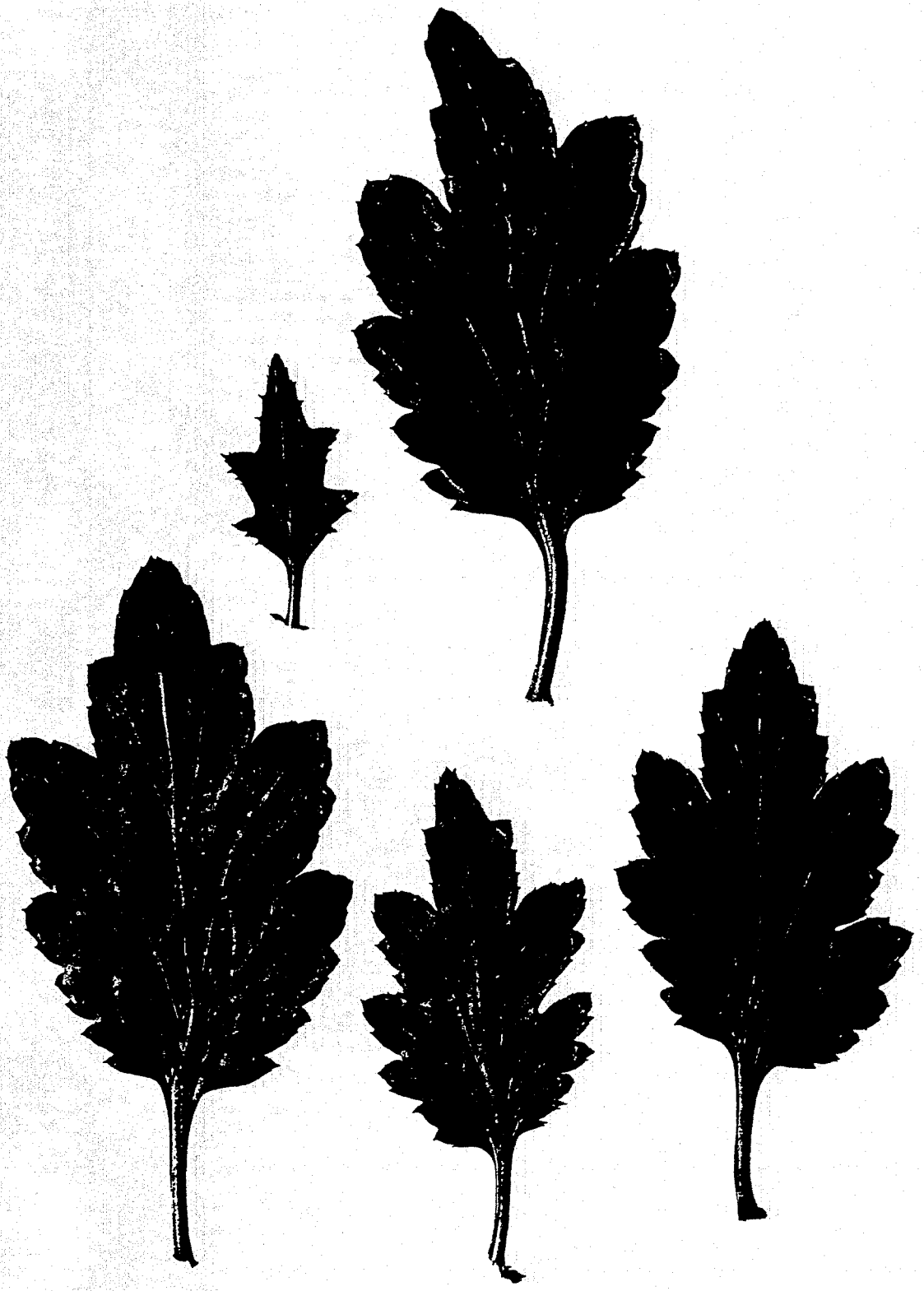

* * * * *